United States Patent [19]

Taylor

[11] 4,105,677

[45] Aug. 8, 1978

[54] PRODUCTION OF TETRAHYDROFURAN

[75] Inventor: Paul D. Taylor, Clinton, N.J.

[73] Assignee: Celanese Corporation, New York, N.Y.

[21] Appl. No.: 681,355

[22] Filed: Apr. 29, 1976

[51] Int. Cl.² ........................................ C07D 307/08
[52] U.S. Cl. .............................................. 260/346.11
[58] Field of Search ......... 260/635 A, 635 E, 346.1 R

[56] References Cited

U.S. PATENT DOCUMENTS

| | | | |
|---|---|---|---|
| 2,251,835 | 8/1941 | Reppe et al. | 260/346.1 R |
| 2,888,492 | 5/1959 | Fischer et al. | 260/635 |
| 3,929,915 | 12/1975 | Cumbo et al. | 260/635 E |
| 3,954,877 | 5/1976 | Gipson | 260/604 HF |
| 4,044,059 | 8/1977 | Copelin | 260/346.11 |

*Primary Examiner*—Henry R. Jiles
*Assistant Examiner*—Bernard Dentz

[57] ABSTRACT

This invention provides a process for producing tetrahydrofuran by (1) the condensation of 2-methyl-1,3-propanediol with acrolein to form 2-vinyl-5-methyl-1,3-dioxane; (2) the conversion of the 2-vinyl-5-methyl-1,3-dioxane under hydroformylation conditions to 3-(5'-methyl-1',3'-dioxane)propionaldehyde; and (3) hydrogenation of the propionaldehyde derivative under acidic conditions to yield tetrahydrofuran.

3 Claims, 1 Drawing Figure

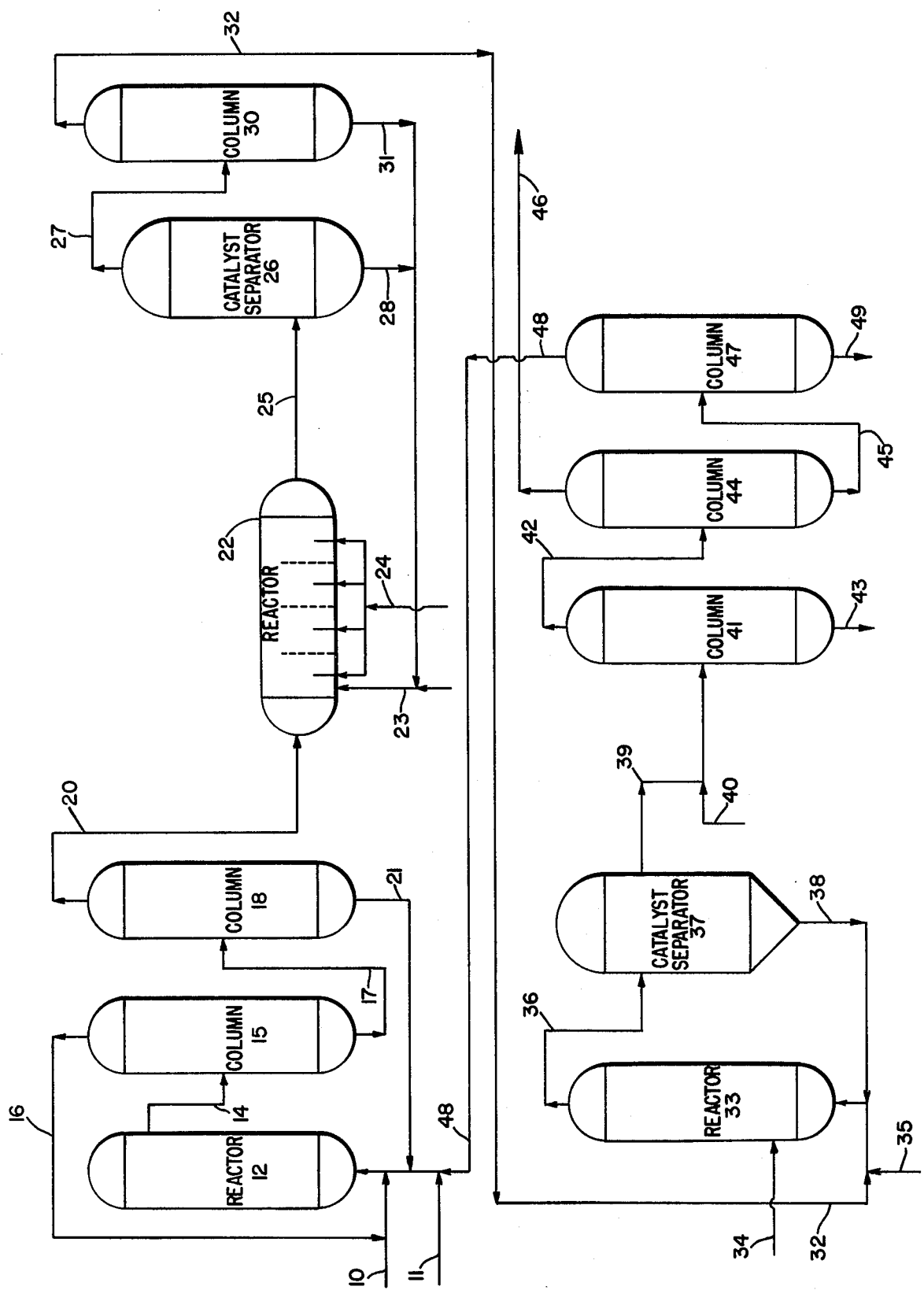

PRODUCTION OF TETRAHYDROFURAN

BACKGROUND OF THE INVENTION

Tetrahydrofuran is an important organic commodity which finds application as a versatile solvent medium and as an intermediate for the production of resins and other commercial products such as butyrolactone and succinic acid.

Tetrahydrofuran can be produced by catalytic hydrogenation of maleic anhydride or furan, as is described in patent literature such as U.S. Pat. Nos. 2,772,293; 2,846,449; 3,021,342; and references cited therein.

It is well known that tetrahydrofuran can be produced by a series of reactions starting with the reaction of aqueous formaldehyde and acetylene in the presence of a cuprous acetylide complex to form butynediol. An alkaline material such as the carbonate, bicarbonate or hydroxide of an alkali or alkaline earth metal is commonly added to this reaction to control pH. This alkaline material generally reacts with the formic acid generated in this reaction to form the metal formate. The product of this reaction is the passed to a hydrogenation step where the butynediol is converted to 1,4-butanediol.

The aqueous product stream from the hydrogenator is then concentrated to form a 1,4-butanediol feed stream typically containing about 3 percent water, about 95-96 percent 1,4-butanediol, and about 0.5-2 percent combined high boiling organic tars and alkali metal or alkaline earth metal salts. The 1,4-butanediol is then converted to tetrahydrofuran employing about 10 percent sulfuric acid. This reaction is conducted under temperature conditions which permit recovery of tetrahydrofuran and water overhead from the reactor. The reaction medium in the reactor typically contains about 50-60 percent unconverted 1,4-butanediol, about 10 percent acid, about 10 percent water, and about 25 percent combined tars and acids. The build-up of tars and salts in the reactor is an undesirable characteristic of this type of process.

There is a need for new and improved commercial processes for the large volume production of tetrahydrofuran. The development of such processes is under active investigation.

Accordingly, it is an object of the present invention to provide a new and efficient method for producing tetrahydrofuran.

It is another object of the present invention to provide an economically feasible continuous process for converting acrolein into tetrahydrofuran on a commercial scale.

Other objects and advantages shall become apparent from the accompanying description and examples.

DESCRIPTION OF THE INVENTION

One or more objects of the present invention are accomplished by the provision of a process for producing tetrahydrofuran which comprises (1) condensing 2-methyl-1,3-propanediol with acrolein to form 2-vinyl-5-methyl-1,3 dioxane; (2) converting the 2-vinyl-5-methyl-1,3-dioxane under hydroformylating conditions to a mixture of 2(5'-methyl-1',3'-dioxane)propionaldehyde and 3-(5'-methyl-1',3'-dioxane)propionaldehyde; and (3) hydrogenating said mixture of propionaldehydes in the presence of a hydrogenation catalyst and water in a reaction medium having a pH between about 0.1 and 5 to yield tetrahydrofuran and 2-methyl-1,3-propanediol.

First Step Condensation Reaction

2-Vinyl-5-methyl-1,3-dioxane starting material is provided by condensation of acrolein with 3-methyl-1,3-propanediol in accordance with conventional procedures:

CH₃—CH(CH₂OH)(CH₂OH) +

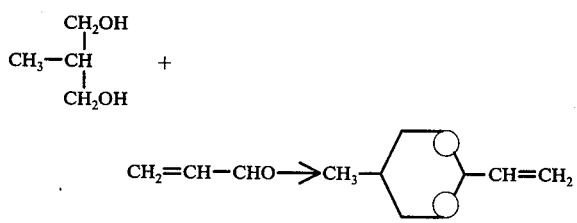

CH₂=CH—CHO⟶CH₃—[dioxane ring]—CH=CH₂

The synthesis of acyclic and cyclic acetals are described in the chemical literature, and in patent literature such as U.S. Pat. Nos. 2,678,950; 2,888,492; 2,915,530, 2,987,524; 3,014,924; and the references cited therein.

Conventional processes for the direct condensation of alpha,beta-unsaturated aldehydes and polyols in the presence of acid catalysts yield large portions of impurities, principally beta-alkoxyacetals and beta-alkoxyaldehydes which are formed by the addition of the polyols across the alpha, beta-double bond of the aldehydes. As a consequence of these undesirable side reactions, attempts have been made to prevent the formation of the aforementioned impurities by reducing the temperature and catalyst concentration; however, these modifications lead to impractically low rates of reaction.

To overcome the disadvantages of conventional processes, U.S. Pat. No. 3,014,924 proposes reacting an alpha, beta-unsaturated aldehyde with an aliphatic polyol bearing at least two hydroxyl groups bonded to different atoms in the polyol molecule in the presence of a catalyst comprising a highly-porous solid carrier having a surface area of at least 75 square meters per gram and about 0.025 to 1.0 millimole per unit weight of carrier of a strong mineral acid.

One convenient method for preparing the catalysts is to first form a slurry in water or other suitable vehicle of the carrier. An amount of mineral acid sufficient to give the desired weight of acid per unit weight of carrier is added to the slurry. Finally, the water is evaporated and the catalyst is dried at elevated temperature (e.g., at 100° to 150° C.) for several hours.

Suitable mineral acids include phosphoric acid, hydrobromic acid, hydrochloric acid and sulfuric acid. Orthophosphoric acid is particularly preferred because, in combination with the carrier, it provides a high yield at a high rate with a minimum of residue.

Highly-porous silica-alumina gel-type structures such as those prepared by precipitating and calcining an alumina hydrogel with or on a precipitated silica hydrogel are preferred. Other suitable carriers include, for example, silica gel, keiselguhr, diatomaceous earth and porous structures of alumina, silica and various combinations thereof with oxides of zirconium, thorium, chromium and the like. The preferred carriers have some catalytic activity in themselves and, although they are not suitable per se, in combination with the afore-mentioned mineral acids they provides particularly high rates and high yields and a minimum of side reactions.

Preferably, 3-methyl-1,3-propanediol and catalyst are added to a suitable reaction vessel together with a water-immiscible solvent which forms an azeotrope with water and the acrolein. Next, the acrolein is added slowly to the reaction mixture. During the reaction, water and unreacted acrolein and azeotroping agent are continuously distilled; the water is separated, then the azeotroping agent and acrolein are returned to the reaction vessel. Preferably the azeotroping agent is at least partially miscible with both reactants. Such preferred agents are, for example, xylene, toluene, benzene, cyclohexane, chloroform, diisobutylene, and hexane.

U.S. Pat. No. 2,888,492 describes a process for producing cyclic acetals which involves reacting an acrolein type aldehyde with a polyol in the presence of 0.02 and 0.06 mole percent based on the amount of ethylenic aldehyde present in a sulfo acid such as sulfuric acid, p-toluenesulfonic acid, ethanesulfonic acid, and the like. The reaction is carried out conveniently by heating a mixture of the chosen alpha, beta-ethylenic aldehyde and polyol, preferably containing about 5 to 50% excess of aldehyde over the stoichiometric requirements for the reaction, dissolved or suspended in a suitable liquid such as benzene, dichloroethylene, and the like. By refluxing at about 50° to 90° C under a phase-separating head until the theoretical amount of water is removed, the reaction is completed in about 1 to 3 hours and high yields of unsaturated cyclic acetals are obtained.

Second Step Hydroformylation Reaction

The present invention process step (2) for reacting 2-vinyl-1,3-dioxane with hydrogen and carbon monoxide under hydroformylation conditions is conducted in the presence of a hydroformylation catalyst.

The preparation of aldehydes and alcohols by the reaction of an olefin with hydrogen and carbon monoxide in the presence of a catalyst is well known in the art, i.e., the "oxo" or "Roelen" reaction. The reaction of an olefin with carbon monoxide and water employing cobalt carbonyl, nickel carbonyl or iron carbonyl is known to produce carboxylic acids (see U.S. Pat. Nos. 2,448,368 and 2,593,440). The reaction of an olefin with carbon monoxide and water produces alcohols when conducted in the presence of an iron carbonyl tertiary amine complex catalyst [Reppe synthesis; Liebig's Ann. Chem., 582, 133 (1953)].

Cobalt catalysts for hydroformylation of olefins to produce alcohols and aldehydes are described in Kirk-Othmer, Encyclopedia of Chemical Technology, 14, 373, second Ed. Cobalt catalysts are also reviewed in "Catalysis Reviews," 6, 85–131 (1972), published by M. Dekker Inc.

For the purpose of the present invention it has been found that superior results are achieved if the hydroformylation reaction is conducted in the presence of a catalyst which is a complex of a Group VIII metal and ligand containing phosphorus, arsenic and/or antimony elements. Tertiary amines can also be employed as a ligand in the catalyst complex.

Catalysts which are suitable for the purposes of the present invention hydroformylation process are illustrated by those described in U.S. Pat. Nos. 3,168,553; 3,239,556; 3,239,570; 3,290,379; 3,369,050; 3,420,898; 3,488,296; 3,527,818; 3,725,534; 3,816,337; 3,821,311; 3,825,601; 3,847,997; 3,857,990; 3,859,369; and the like.

Any of the metal-phosphine complexes disclosed in "Carbon Monoxide in Organic Synthesis," Falbe, (Springer-Verlag 1970), pages 14–25, may be used. The preferred catalysts are phosphine complexes of rhodium, cobalt, iridium and ruthenium. The most preferred catalysts have the formula $RhCOH(Q_3P)_3$, $RhCOH[(QO)_3P]_3$, $RHCOCl[(QO)_3P]_2$ and $RhCOCl(Q_3P)_2$ wherein Q is phenyl; alkyl substituted cyclohexyl such as methyl, propyl, octyl, and the like; substituted cyclohexyl; and aliphatic radical such as methyl, butyl, octyl, and the like, or mixtures of any of the foregoing, preferably phenyl. Rhodium catalysts containing tertiary amines are also important hydroformylation catalysts, e.g., a catalyst complex of rhodium metal, carbon monoxide, and a trialkyl amine, triaryl amine or trialkylaryl amine.

The step (2) 3-(5'-methyl-1',3'-dioxane)propionaldehyde reaction product can be provided in a high yield selectivity of at least 70 weight percent by reacting 2-vinyl-5-methyl-1,3-dioxane with hydrogen and carbon monoxide in the presence of a hydroformylation catalyst at a temperature between about 25° and 200° C and a pressure between about 15 and 300 psi.

Illustrative of a preferred embodiment of the step (2) hydroformylation reaction, 3-(5'-methyl-1',3'-dioxane)-propionaldehyde is produced in a yield of at least 80 weight percent by reacting 2-vinyl-5-methyl-1,3-dioxane with hydrogen and carbon monoxide in the presence of a metal-ligand complex hydroformylation catalyst at a temperature between 80° and 120° C and a pressure between about 75 and 150 psi. The relative amounts and hydrogen and carbon monoxide employed can vary in accordance with conventional hydroformylation processes, i.e., a molar ratio between 10:1 and 1:10. It has been observed that a high yield of 3-(5'-methyl-1',3'-dioxane)propionaldehyde is favored by increasing the relative ratio of hydrogen to carbon monoxide. Hence, to achieve the conversion of 2-vinyl-5-methyl-1,3-dioxane to 3-(5'-methyl-1',3'-dioxane)propionaldehyde in a yield of 85 weight percent and higher, a molar ratio of 1:2 to 2:1 of hydrogen to carbon monoxide is employed in the presence of a hydroformylation catalyst which is a complex of a Group VIII metal and a ligand containing phosphorus, arsenic and/or antimony elements.

The hydroformylation catalyst is generally employed in a quantity between about 0.001 and 5 weight percent, based on the weight of vinyl(1,3-dioxane) starting material, and preferably a weight percent quantity between about 0.01 and 1.0, exclusive of the weight of the ligand if present.

The hydroformylation reaction can be carried out in a solvent, preferably one which is inert with respect to the products or starting materials. The solvent generally dissolves the catalyst, starting material and products. It is also possible to use the reaction products as the solvent. The latter is a commonly employed industrial expedient. A wide variety of organic solvents such as, for example, aromatics, aliphatics, esters, ethers, nitriles, alcohols, halogenated hydrocarbons, and the like, including benzene, cyclohexane, ethyl acetate, methyl alcohol, ethyl orthoformate, tetrahydrofuran, dioxane, isopropyl alcohol, aliphatic hydrocarbon cuts (saturated), chlorobenzene, methylene chloride, propionitrile, acetonitrile, trimethyl acetonitrile, and the like, and mixtures thereof may be employed.

For the operation of the hydroformylation reaction on a large scale, it is advantageous to exclude any solvent from the reaction medium. Excellent results can be achieved, for example, by employing a rhodium carbonyl catalyst component which is incorporated in a large excess of triphenyl phosphine. The said triphenyl phosphine can be included in the reaction medium in a quantity which is between 20 and 90 percent of the total weight of catalyst and a vinyl(1,3-dioxane) reactant. Triphenyl phosphine at a temperature above about 80° C is highly fluid and performs as an excellent medium for the invention process.

If desired, the hydroformylation reaction can be conducted under conditions which are selected to yield an alcohol derivative rather than an aldehyde derivative for use as a step (2) reaction product in the present invention process. Hence, what is contemplated is a process which comprises (1) reacting 2-vinyl-5-methyl-1,3-dioxane with hydrogen and carbon monoxide in the presence of a metal-ligand complex hydroformylation catalyst at a temperature between about 80° and 120° C and a pressure between about 300 and 3000 psi to form 3-(5-methyl-1',3'-dioxane)propionaldehyde; and (2) increasing the temperature to above about 150° C to convert said 3-(5'-methyl-1',3'-dioxane) propionaldehyde to 3-(5'-methyl-1',3'-dioxane)propanol.

A preferred class of catalyst for the two-step process for producing 3-(5'-methyl-1',3'-dioxane)propanol derivatives are cobalt metal hydroformylation catalysts which are phosphine-modified. A suitable catalyst for such a process is a complex of cobalt metal, carbon monoxide, and trialkyl phosphine (e.g., tributyl phosphine).

The temperature in the second step of the process is maintained in the range between about 150° and 225° C, and preferably at about 190° C. The pressure in the hydroformylation system is maintained in the range between about 300 and 3000 psi, and preferably between about 500 and 1000 psi.

2-vinyl-5-methyl-1,3-dioxane when subjected to the selected hydroformylation conditions described hereinabove for the two-step process yields a mixture of 3-(5'-methyl-1',3'-dioxane)propanol and 2-(5'-methyl-1',3'-dioxane)propanol:

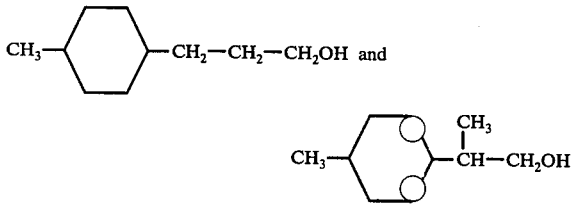

As it is apparent, the two-step hydroformylation process can be moderated to yield a mixture of aldehyde and alcohol derivatives as the product of the process. Also, the two-step process can be operated as a one-step process by maintaining the initial temperature above about 150° C rather than in the range of 80° to 120° C. At elevated temperatures, the vinyldioxane starting material is more susceptible to hydrogenation to the corresponding ethyldioxane derivative.

Third Step Hydrogenation Reaction

The invention process step (3) hydrogenation reaction for converting 3-(5'-methyl-1',3'-dioxane)propionaldehyde into tetrahydrofuran is conducted in the presence of a hydrogenation catalyst in an aqueous medium having a pH between about 0.1 and 5.0. Maintenance of the reaction medium within the specified acidic range of pH is an important feature of the invention process.

In accordance with a preferred embodiment of the present invention process for producing tetrahydrofuran, 3-(5'-alkyl-1',3'-dioxane)propionaldehyde and/or 3-(5'-alkyl-1',3'-dioxane)propanol and/or 4-hydroxybutanal is contacted with hydrogen in the presence of a hydrogenation catalyst and water in a reaction medium maintained at a pH in the range between about 0.2 and 3, and at a temperature between about 150° and 250° C and a pressure between about 15 and 1500 psi.

The hydrogenation catalysts suitable for use include metal catalysts such as platinum, palladium, silver, copper, vanadium, tungsten, cobalt, nickel, iron, ruthenium, rhodium, maganese, chromium, molybdenum, iridium, zirconium, and the like, and mixtures of the same and compounds and alloys thereof as described in prior art such as U.S. Pat. No. 2,840,617.

The hydrogenation catalyst can be employed in a finely divided form as a dispersion throughout the reaction medium. Or, the catalyst may be employed in the form of beads or pellets and the like, either in a pure state or supported upon or carried by an inert or catalytically active supporting or carrier material such as pumice, kieselguhr, diatomaceous earth, clay, alumina, charcoal, carbon, or the like. In the latter type supported hydrogenation catalysts, the reaction medium is contacted therewith by flowing the reaction medium over or through a bed of the catalyst, or by other contacting means known in the art.

The quantity of hydrogenation catalyst employed can vary over a broad weight range depending on the nature of the starting material and other processing conditions. For a batch type process, the quantity of hydrogenation catalyst normally can range between 1 and 30 weight percent, based on the weight of dioxane starting material, and preferably is in the range between about 1 and 10 weight percent.

The presence of water is required in the present invention process to achieve the hydrolysis-hydrogenation reaction mechanism which theoretically is involved. The quantity of water employed is at least the stoichiometric amount required to interact hydrolytically with the dioxane reactant. Preferably, the quantity of water in the reaction medium will vary between about one mole and 10 moles per mole of dioxane reactant, in a manner analogous to that described in U.S. Pat. No. 2,888,492.

The invention process preferably is conducted at a temperature in the range between about 180° and 225° C, and at a hydrogen pressure in the range between about 100 and 1000 psi.

It is an essential requirement of the present invention process that the pH of the reaction medium be maintained within the range between about 0.1 and 5, preferably in the pH range between 0.2 and 3. The conversion of 3-(5'-alkyl-1',3'-dioxane)propionaldehyde and/or 3-(5'-alkyl-1',3'-dioxane)propanol can be accomplished essentially quantitatively if the pH of the reaction medium is maintained in the preferred range, i.e., a pH range between about 0.2 and 3. The yield of tetrahydrofuran product diminishes as the pH of the reaction medium increases in basicity. If the pH of the reaction medium is in the range between about 5 and 7.5 then 1,4-butanediol is obtained as the main product instead of tetrahydrofuran. If the pH of the reaction medium is above 10, then the 3-(5'-alkyl-1',3'-dioxane)propionaldehyde starting material undergoes diverse condensationpolymerization type reactions, and no tetrahydrofuran product is recoverable.

The pH of the reaction medium is conveniently maintained in the acidic range of pH by the addition of an appropriate quantity of a mineral acid such as sulfuric acid, or an organic acid such as acetic acid or p-toluenesulfonic acid. A polycarboxylic acid or an acidic ion-exchange resin may also be employed if desired. In the case of copper, nickel or iron catalysts, it is advantageous to employ a carboxylic acid as the acid component of the reaction mixture so as to maintain a high level of catalytic activity.

At the conclusion of the present invention hydrogenation process, the tetrahydrofuran product can be recovered directly from the reaction product mixture by conventional procedures. The hydrogenation catalyst if dispersed as fine powder, can be removed by filtration, centrifugation, or by other suitable means. For commercial scale operation, the process is preferably conducted as a continuous operation, and the catalyst, dioxane starting material, and 2-alkyl-1,3-propanediol by-product of the process are recycled in an appropriate manner.

Continuous Process

The accompanying drawing is a schematic representation of the invention process for converting acrolein into tetrahydrofuran as a continuous operation.

Referring to the drawing, acrolein is fed through line 10 and combined with 2-methyl-1,3-propanediol which is fed through line 11 to reactor 12 containing an acid catalyst, such as iron exchange resin at 60°–90° C, to produce 2-vinyl-5-methyl-1,3-dioxane. The reaction mixture is passed through line 14 into column 15. The unreacted acrolein and product water is separated in column 15 as an overhead stream. This stream is separated and the acrolein recycled through line 16. The bottoms from column 15 contain acrolein acetal and unreacted 2-methyl-1,3-propanediol which are passed through line 17 and separated in column 18. The 2-vinyl-5-methyl-1,3-dioxane is withdrawn from column 18 as an overhead stream through line 20. 2-Methyl-1,3-propanediol is withdrawn as a bottoms stream and recycled through line 21. The 2-vinyl-5-methyl-1,3-dioxane is hydroformylated in reactor 22 with a rhodium/-triphenylphosphine catalyst which is introduced through line 23. Carbon monoxide and hydrogen are sparged into reaction 22 through line system 24. The effluent from reactor 22 passes through line 25 to catalyst separator 26 where 3-(5'methyl-1',3'-dioxane)propionaldehyde is withdrawn through line 27 as an overhead stream with some triphenylphosphine, and the catalyst is withdrawn as a bottom stream which is recycled through line 28. The 3-(5'-methyl-1',3'-dioxane)propionaldehyde stream containing small amounts of triphenylphosphine is further separated in column 30. A bottoms stream containing mainly triphenylphosphine is recycled through line 31. An overhead stream of 3-(5'-methyl-1',3'-dioxane)propionaldehyde is passed through line 32 to reactor 33. The feed stream from line 32 is mixed in reactor 33 with a water diluted mineral acid introduced through line 34 and with a hydrogenation catalyst, such as Pd/carbon, and hydrogen which is introduced through line 35. The reactor effluent passes overhead through line 36 to catalyst separator 37, where the hydrogenation catalyst is recovered and recycled through line 38. The effluent from separator 37 passes through line 39 where it is neutralized by the introduction of a small amount of base, such as sodium hydroxide through line 40. The neutralized solution containing water, tetrahydrofuran and 2-methyl-1,3-propanediol is entered into column 41 where the water and THF components are separated and passed as an overhead stream through line 42 into column 44. 2-Methyl-1,3-propanediol is withdrawn from column 41 as a bottom stream through line 43. The THF/water stream 42 is further purified in column 44 where water is separated as a bottom stream through line 45, and THF is withdrawn as an overhead stream through line 46. The bottom stream 45 from column 44 is further separated in column 47 where pure 2-methyl-1,3-propanediol is provided as an overhead stream through line 48 and is recycled to reactor 12, and the neutralized salts are withdrawn as a column 47 bottoms fraction through line 49.

The following examples are further illustrative of the present invention. The reactions and other specific ingredients are presented as being typical, and various modifications can be derived in view of the foregoing disclosure within the scope of the invention.

EXAMPLE I

Preparation Of 2-Vinyl-5-methyl-1,3-dioxane In Accordance With Step (1) Of The Invention Process Acrolein (59.5 grams) and 2-methyl-1,3-propanediol (83.8 grams) were added to benzene (100 grams) and p-toluenesulfonic acid (0.0596 gram) in a 500 ml flask equipped with a Dean-Stark trap, condenser, heating mantle and magnetic stirrer.

The mixture was heated at reflux for 4 hours with continuous removal of the water of reaction. The reaction mixture was cooled, neutralized with calcium oxide, filtered, and distilled to yield 66 grams of 2-vinyl-5-methyl-1,3-dioxane (65 percent yield).

EXAMPLE II

Preparation Of 3-(5'-methyl-1',3'-dioxane)propionaldehyede In Accordance With Step (2) Of The Invention Process A hydroformylation synthesis was conducted in a 300 ml magnetically stirred autoclave in the following manner:

Benzene (60 grams), triphenylphosphine (30 grams), hexarhodium hexadecyl-carbonyl [$Rh_6(CO)_{16}$, 0.20 grams] and 2-vinyl-5-methyl-1,3-dioxane (40 grams) were charged into the autoclave and with stirring heated at 90° C under a constant pressure of 90 psig carbon monoxide/hydrogen (1:1 mole ratio) for 105 minutes.

The reaction mixture was recovered and analyzed by gas chromatography. Analysis indicated that the reaction mixture contained 3-(5'-methyl-1',3'-dioxane)propionaldehyde (95 mole percent, 2-(5'-methyl-1',3'-dioxane)propionaldehyde (4 mole percent) and 2-ethyl-5-methyl-1,3-dioxane (1 mole percent). The overall yield to propionaldehyde was 98 percent.

If cobalt metal-ligand complex hydroformylation catalyst is employed, an additional step of increasing the temperature to above about 150° C and the pressure to above about 500 psi yields the corresponding propanol derivatives.

EXAMPLE III

Conversion Of 3-(5'-Methyl-1',3'-dioxane)propionaldehyde To Tetrahydrofuran In Accordance With Step (3) Of The Invention Process Acrolein and 1,3-butanediol were condensed to produce 2-vinyl-5-methyl-1,3-dioxane in accordance with the procedure of Example I.

2-Vinyl-5-methyl-1,3-dioxane was hydroformulated in accordance with the procedure of Example II to yield a mixture of 3-(5'-methyl-1',3'-dioxane)propionaldehyde (95 mole percent) and 2-(5'-methyl-1',3'-dioxane)propionaldehyde (4 mole percent).

The said mixture of propionaldehydes (5.0 grams), water (44.0 grams), 10% palladium on carbon powder (1.0 gram) and acetic acid (1.0 gram) were charged into a stirred autoclave. The pH of this mixture was 2.7. The reaction mixture was heated to 195° C over a 50 minute period at a hydrogen pressure of 350–435 psig. After the temperature was maintained at 195° C for an additional 15 minutes, the autoclave was cooled to room temperature and the reaction product recovered.

Gas chromatographic analysis indicated that the product mixture was essentially water, acetic acid, 1,3-butanediol and tethydrofuran. Essentially no 1,4-butanediol was detected. The pH of the mixture after the reaction was 2.9.

The same product mixture is produced if the organic starting material in the hydrogenation stage is a mixture of 3-(5'-methyl-1',3'-dioxane)propanol and 2-(5'-methyl-1',3'-dioxane)propanol.

The same product mixture is also produced if the organic starting material being hydrogenated is a mixture of 4-hyroxybutanal and 3-(5'-methyl-1',3'-dioxane)-propionaldehyde and/or 3-(5'-methyl-1',3'-dioxane)-propanol.

Under the same hydrogenation conditions, 4-hydroxybutanal converts in a mixture of tetrahydrofuran 1,4-butanediol.

What is claimed is:

1. A process for converting acrolein into tetrahydrofuran which comprises (1) forming 2-vinyl-5-methyl-1,3-dioxane by the acid-catalyzed condensation of acrolein with 2-methyl-1,3-propanediol; (2) hydroformylation of the 2-vinyl-5-methyl-1,3-dioxane with carbon monoxide and hydrogen in the presence of a hydroformylation catalyst at a temperature between about 25° and 200° C and a pressure between about 15 and 300 psi to produce a mixture of 2-(5'-methyl-1',3'-dioxane)propionaldehyde and 3-(5'-methyl-1',3'-dioxane)propionaldehyde; and (3) hydrogenating said mixture of propionaldehydes with hydrogen in the presence of a hydrogenation catalyst at a temperature between about 180° and 225° C and a pressure between about 100 and 1000 psi in an aqueous medium maintained at a pH between about 0.2 and 3 with a water-soluble acid to produce a product mixture of tetrahydrofuran and 2-methyl-1,3-propanediol, and recovering the tetrahydrofuran from the product mixture.

2. A process for producing tetrahydrofuran which comprises (1) continuously feeding and reacting 2-methyl-1,3-propanediol and acrolein to form 2-vinyl-5-methyl-1,3-dioxane in a condensation reaction zone; (2) continuously withdrawing the 2-vinyl-5-methyl-1,3-dioxane from said condensation reaction zone and continuously feeding the 2-vinyl-5-methyl-1,3-dioxane into a hydroformylation reaction zone to produce a mixture of 2-(5-methyl-1',3'-dioxane)propionaldehyde and 3-(5'-methyl-1',3'-dioxane)propionaldehyde in the presence of a hydroformylation catalyst at a temperature between about 25° and 200° C and a pressure between about 15 and 300 psi; (3) continuously withdrawing the propionaldehyde mixture and catalyst from the hydroformylation reaction zone; (4) continuously separating and recycling the hydroformylation catalyst to the hydroformylation reaction zone; (5) continuously feeding and contacting the propionaldehyde mixture with hydrogen in a hydrogenation zone in the presence of a hydrogenation catalyst at a temperature between about 180° and 225° C and a pressure between about 100 and 1000 psi in an aqueous medium maintained at a pH between about 0.2 and 3 with a water-soluble acid to produce a product mixture of tetrahydrofuran and 2-methyl-1,3-propanediol; (6) continuously recovering the tetrahydrofuran and 2-methyl-1,3-propanediol as separate components; and (7) continuously recycling the 2-methyl-1,3-propanediol to the first step condensation reaction zone.

3. A process for converting acrolein into tetrahydrofuran which comprises (1) forming 2-vinyl-5-methyl-1,3-dioxane by the acid-catalyzed condensation of acrolein with 2-methyl-1,3-propanediol; (2) hydroformylation of the 2-vinyl-5-methyl-1,3-dioxane with carbon monoxide and hydrogen in the presence of a hydroformylation catalyst at a temperature between about 80° and 120° C and a pressure between about 300 and 3000 psi to produce a mixture of 2-(5'-methyl-1',3'-dioxane)-propionaldehyde and 3-(5'-methyl-1',3'-dioxane)propionaldehyde, and increasing the temperature into the range between about 150° and 225° C to convert the propionaldehydes into a mixture of 2-(5'-methyl-1',3'-dioxane)propanol and 3-(5'-methyl-1',3'-dioxane)-propanol; and (3) hydrogenating said mixture of propanols with hydrogen in the presence of a hydrogenation catalyst at a temperature between about 180° and 225° C and a pressure between about 100 and 1000 psi in an aqueous medium maintained at a pH between about 0.2 and 3 with a water-soluble acid to produce a product mixture of tetrahydrofuran and 2-methyl-1,3-propanediol, and recovering the tetrahydrofuran from the product mixture.

* * * * *